(12) United States Patent
Sheldon et al.

(10) Patent No.: US 7,181,268 B2
(45) Date of Patent: Feb. 20, 2007

(54) ISCHEMIA DETECTION

(75) Inventors: Todd J. Sheldon, North Oaks, MN (US); Lee Stylos, Stillwater, MN (US); Shannon D. Nelson, Stacy, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 593 days.

(21) Appl. No.: 10/304,112

(22) Filed: Nov. 25, 2002

(65) Prior Publication Data
US 2003/0158492 A1 Aug. 21, 2003

Related U.S. Application Data

(60) Provisional application No. 60/337,252, filed on Dec. 3, 2001.

(51) Int. Cl.
*A61B 5/0402* (2006.01)
(52) U.S. Cl. ............... 600/513; 600/508; 600/509; 607/17; 607/19
(58) Field of Classification Search ........... 600/509, 600/508, 513; 607/17, 19
See application file for complete search history.

(56) References Cited

U.S. PATENT DOCUMENTS

| | | | |
|---|---|---|---|
| 4,404,974 A * | 9/1983 | Titus ........................ 600/483 |
| 4,693,075 A | 9/1987 | Sabatiuk |
| 5,135,004 A * | 8/1992 | Adams et al. ............. 600/508 |
| 5,159,932 A * | 11/1992 | Zanetti et al. ............ 600/508 |
| 5,304,208 A | 4/1994 | Inguaggiato et al. |
| 5,330,505 A * | 7/1994 | Cohen ........................... 607/6 |
| 5,365,426 A * | 11/1994 | Siegel et al. ............. 600/509 |
| 5,454,838 A | 10/1995 | Vallana et al. |
| 5,480,412 A * | 1/1996 | Mouchawar et al. ......... 607/6 |
| 5,496,351 A | 3/1996 | Plicchi et al. |
| 5,531,768 A * | 7/1996 | Alferness ...................... 607/6 |
| 5,609,612 A | 3/1997 | Plicchi et al. |
| 5,693,075 A | 12/1997 | Plicchi et al. |
| 5,795,303 A * | 8/1998 | Swanson et al. .......... 600/509 |
| 5,833,713 A * | 11/1998 | Moberg ..................... 607/19 |
| 6,002,963 A * | 12/1999 | Mouchawar et al. ........ 607/18 |
| 6,009,349 A * | 12/1999 | Mouchawar et al. ......... 607/6 |

(Continued)

FOREIGN PATENT DOCUMENTS

| | | |
|---|---|---|
| EP | 0 467 695 A2 | 1/1992 |
| WO | WO 97/24981 A2 | 7/1997 |
| WO | WO 99/26693 A1 | 6/1999 |

*Primary Examiner*—Robert E. Pezzuto
*Assistant Examiner*—Deborah Malamud
(74) *Attorney, Agent, or Firm*—Girma Wolde-Michael; Paul H. McDowall

(57) ABSTRACT

Techniques for detection and treatment of myocardial ischemia are described that monitor both the electrical and dynamic mechanical activity of the heart to detect and verify the occurrence of myocardial ischemia in a more reliable manner. The occurrence of myocardial ischemia can be detected by monitoring changes in an electrical signal such as an ECG or EGM, and changes in dynamic mechanical activity of the heart that are sensed by an accelerometer sensor. The heart acceleration signal can be obtained from an single- or multiple-axis accelerometer and/or a pressure sensor deployed within or near the heart. The techniques correlate contractility changes detected by an accelerometer or pressure sensor with changes in the ST electrogram segment detected by the electrodes to increase the reliability of ischemia detection.

14 Claims, 10 Drawing Sheets

U.S. PATENT DOCUMENTS

| | | |
|---|---|---|
| 6,010,477 A | 1/2000 | Bays |
| 6,016,443 A | 1/2000 | Ekwall et al. |
| 6,021,350 A | 2/2000 | Mathson |
| 6,024,705 A * | 2/2000 | Schlager et al. ............ 600/508 |
| 6,038,469 A * | 3/2000 | Karlsson et al. ............ 600/512 |
| 6,077,236 A | 6/2000 | Cunningham |
| 6,077,277 A | 6/2000 | Mollenauer et al. |
| 6,128,526 A | 10/2000 | Stadler et al. |
| 6,171,256 B1 | 1/2001 | Joo et al. |
| 6,217,525 B1 * | 4/2001 | Medema et al. ............ 600/508 |
| 6,449,508 B1 * | 9/2002 | Sheldon et al. ............ 607/19 |
| 6,937,899 B2 * | 8/2005 | Sheldon et al. ............ 607/18 |

* cited by examiner

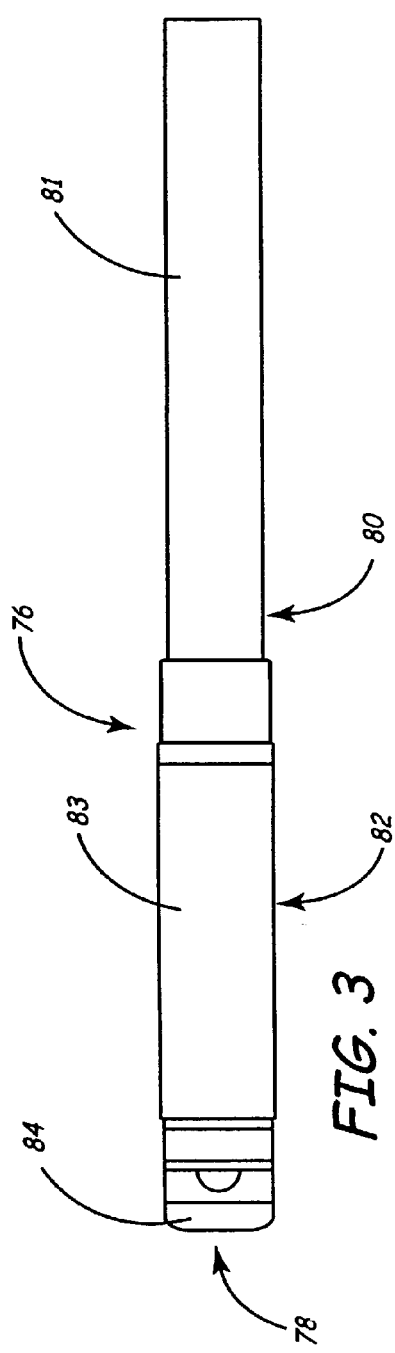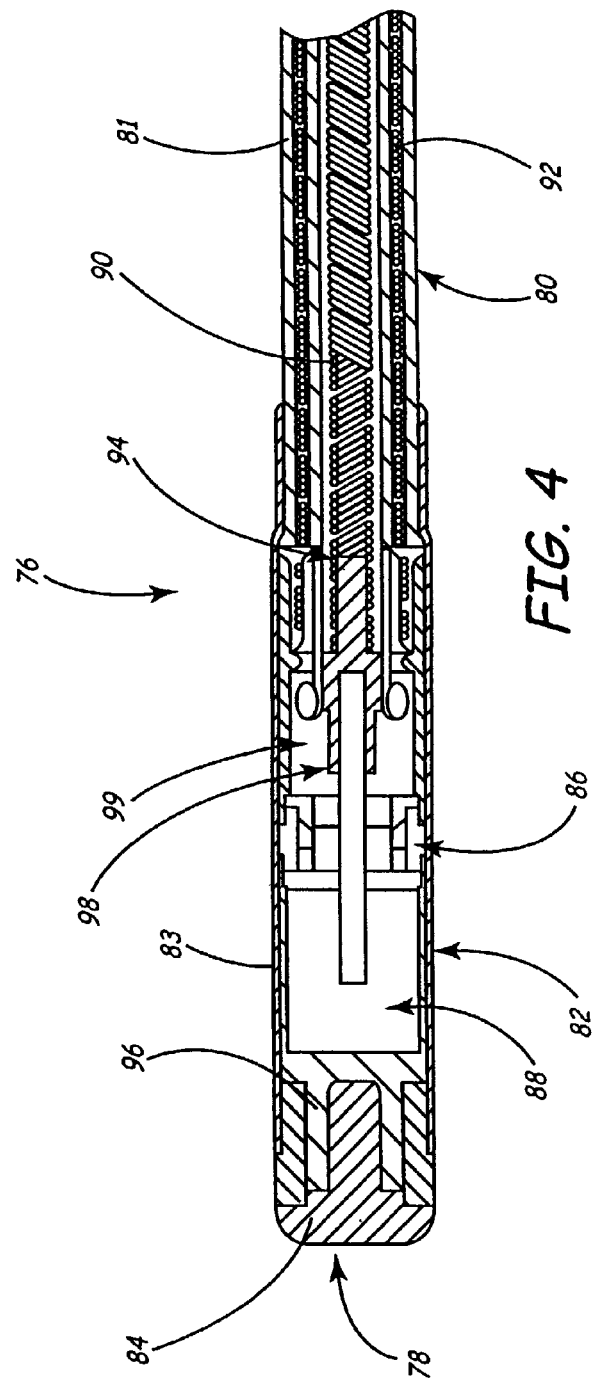

ISCHEMIA DETECTION

CROSS-REFERENCE TO RELATED APPLICATIONS

This patent application claims the benefit of provisional U.S. patent application No. 60/337,252 filed Dec. 3, 2001 and entitled, "Ischemia Detection" invented by Sheldon et al. The Applicant incorporates the contents of said provisional U.S. patent application by reference herein and claims priority thereto.

FIELD OF THE INVENTION

The invention relates to cardiac health and, more particularly, to techniques for detection of myocardial ischemia.

BACKGROUND OF THE INVENTION

Myocardial ischemia, a leading cause of mortality, involves oxygen starvation of the myocardium. Myocardial ischemia can lead to myocardial infarction if left untreated. Early detection of myocardial ischemia provides the opportunity for a wide range of effective therapies such as surgical revascularization, neural stimulation, and drug delivery to reduce cardiac workload or improve cardiac circulation. Unfortunately, many episodes of myocardial ischemia do not cause excessive pain or other noticeable warning signs, and often go undetected.

An electrocardiogram (ECG) or electrogram (EGM) presents a PQRST waveform sequence that characterizes the cyclical cardiac activity of a patient. The T-wave can be used to identify an ischemic condition. U.S. Pat. No. 6,016,443 to Ekwall et al., for example, describes an implantable ischemia detector that employs a repolarization sensor and a patient workload sensor to identify ischemic episodes. The repolarization sensor detects T-wave amplitude or duration to identify increased heart rate. The workload sensor detects patient activity such as exercise by monitoring body movement, muscle sounds, fluid pressure waves, or metabolic changes. When the T-wave indicates an increased heart rate, without a corresponding increase in workload, the detector identifies an ischemic condition.

The ST segment, also associated with the repolarization of the ventricles, is typically close in amplitude to the baseline, i.e., isoelectric amplitude, of the signal sensed between consecutive PQRST sequences. During episodes of myocardial ischemia, the ST segment amplitude deviates from the baseline. Accordingly, deviation in the ST segment is often used to identify an occurrence of myocardial ischemia.

U.S. Pat. No. 6,021,350 to Mathson, for example, describes an implantable heart stimulator having an ischemia detector that indicates an ischemic condition based on elevation of the ST-segment above a baseline. Alternatively, the ischemia detector may rely on a measure of heart activity or patient workload. The stimulator controls the rate of stimulation based on the detection of ischemia using either of the alternative detection modes.

Unfortunately, the use of the ST segment as an indicator of ischemia can be unreliable. The ST segment may deviate from the baseline due to other factors, causing false indications of myocardial ischemia. For example, the ST segment may deviate from the baseline due to changes in the overall PQRST complex, possibly caused by axis shifts, electrical noise, cardiac pacing stimuli, drugs and high sinus or tachycardia rates that distort the PQRST complex. Consequently, the reliability of the ST segment as an indicator of myocardial ischemia can be uncertain.

U.S. Pat. No. 6,128,526 to Stadler et al. describes an ischemia detector that observes variation in the ST segment to identify an ischemic condition. To improve reliability, the detector is designed to filter out ST segment variations caused by factors other than ischemia, such as axis shift, electrical noise, cardiac pacing, and distortion in the overall PQRST complex.

Efforts to verify the reliability of the ST segment have generally proven complicated. Accordingly, there continues to be a need for a simplified system capable of automatically and reliably detecting myocardial ischemia.

SUMMARY OF THE INVENTION

The invention is directed to techniques for more reliable detection and treatment of myocardial ischemia. In particular, the invention correlates electrical activity and dynamic mechanical activity of a heart to detect and verify the occurrence of myocardial ischemia in a more reliable manner.

The electrical activity may be represented by the ST segment. The dynamic mechanical activity may be represented by a heart acceleration or pressure signal. Heart acceleration or pressure provides an indication of heart contractility. The term "contractility" generally refers to the ability of the heart to contract, and may indicate a degree of contraction. Heart contractility typically decreases during ischemic episodes.

Accordingly, the invention determines whether a change in the ST segment is accompanied by a corresponding change in the contractility of the heart. Correlation of changes in the contractility of the heart with changes in the ST segment provides a more reliable indication of ischemia, reducing the incidence of false indications due to ST segment changes that are unrelated to ischemic conditions.

Changes in the ST segment can be detected from an ECG, EGM, or subcutaneous electrode array (SEA). Changes in the dynamic mechanical activity of the heart can be obtained from an accelerometer or pressure transducer. The accelerometer produces an acceleration signal indicative of heart wall acceleration within a chamber of the heart. The pressure transducer produces a pressure signal indicative of right ventricular, left ventricular, or arterial pressure, depending upon the location of the pressure transducer.

For the ST segment, the electrical signal can be obtained from a set of implanted or external electrodes. For dynamic heart activity, an accelerometric signal can be obtained from an accelerometer deployed within or near the heart. The accelerometer transduces heart contractions into one or more accelerometric signals. The pressure signal can be obtained from a pressure transducer deployed within the heart or vasculature. Alternately, the pressure sensor could be positioned around a blood vessel.

The accelerometer can be disposed at the distal tip of an implanted lead that is deployed within a chamber of the heart. The pressure transducer can be realized by a cardiac pressure lead. A signal processing circuit can be used to detect drops in contractility during myocardial ischemia by comparing the accelerometric or pressure signal to a criterion such as a predetermined threshold.

The invention correlates contractility changes derived from signals generated by a lead tip accelerometer or cardiac pressure lead with changes in the ST segment to increase the specificity of ischemia detection. In particular, the utilization of a lead tip accelerometer or pressure lead in conjunction with electrical detection permits differentiation between ST segment changes accompanied by changes in cardiac contractility and ST segment changes without significant changes in cardiac contractility. Changes in cardiac contractility derived from the accelerometer or pressure lead provide another indication of ischemic conditions, and confirm the indication provided by the ST segment.

In one embodiment, the invention provides a method for detecting myocardial ischemia, the method comprising obtaining a first signal indicative of dynamic mechanical activity of a heart, obtaining a second signal indicative of electrical activity of the heart, and detecting myocardial ischemia based on both the first signal and the second signal. The invention also may provide computer-readable media carrying instructions for performing the method.

In another embodiment, the invention provides a system for detecting myocardial ischemia, the system comprising a first sensor that generates a first signal indicative of dynamic mechanical activity of a heart, a second sensor that obtains a second signal indicative of electrical activity of the heart, and a processor that detects myocardial ischemia based on both the first signal and the second signal.

In an added embodiment, the invention provides a method for detecting myocardial ischemia, the method comprising obtaining a first signal indicative of contractile activity of a heart, obtaining a second signal indicative of electrical activity of the heart, and detecting myocardial ischemia based on both the first signal and the second signal. The invention also may provide computer-readable media carrying instructions for performing the method.

In a further embodiment, the invention provides a system for detecting myocardial ischemia, the system comprising means for generating a first signal indicative of contractile activity of a heart, means for obtaining a second signal indicative of electrical activity of the heart, and means for detecting myocardial ischemia based on both the first signal and the second signal.

In yet a further embodiment, myocardial ischemia detection was based solely on a peak endocardial acceleration (PEA) signal. In this form of the invention, PEA is defined as the peak-to-peak change in accelerometer signal measured 100 ms after the R-wave was detected, although definitions may be employed within the scope of this form of the invention. In this form of the invention, PEA may be used a surrogate for LV dp/dt to assess changes in global contractility of a heart during paced rhythm. Thus, PEA may be measured periodically and such measurements compared and the results then provide said global contractility changes.

The invention is capable of providing a number of advantages. For example, correlation of changes in heart contractility with changes in the ST segment provide a more reliable indication of an ischemic event. In this manner, the invention is useful in increasing the specificity of ischemia detection, generally avoiding false indication of ischemic events due to axis shifts, electrical noise, cardiac pacing stimuli, high sinus or tachycardia rates, or other factors that undermine the effectiveness of a purely electrical detection technique. Also, the invention is capable of improving sensitivity to ischemic episodes by allowing the detection of ischemia when either the mechanical or the electrical signals are indicative of ischemia.

In addition, the invention can be useful in quantifying a degree of ischemic tissue according to a degree of cardiac contractility and a degree of change in the ST segment. Moreover, the combination of electrical and mechanical monitoring of heart activity can aid in determining the location of ischemic tissue. In particular, both the electrical and mechanical signals can be monitored along multiple axes. The electrical signal may include multiple electrical signals obtained from different lead sets, whereas an accelerometer may be sensitive along two and perhaps three axes. Likewise, multiple accelerometers or pressure sensors can be used to achieve sensitivity along multiple axes.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 3 is a side view illustrating an implantable lead suitable for incorporation of a lead-tip accelerometer.

FIG. 4 is a cross-sectional side view of the lead shown in FIG. 3.

DETAILED DESCRIPTION

Figure 1:
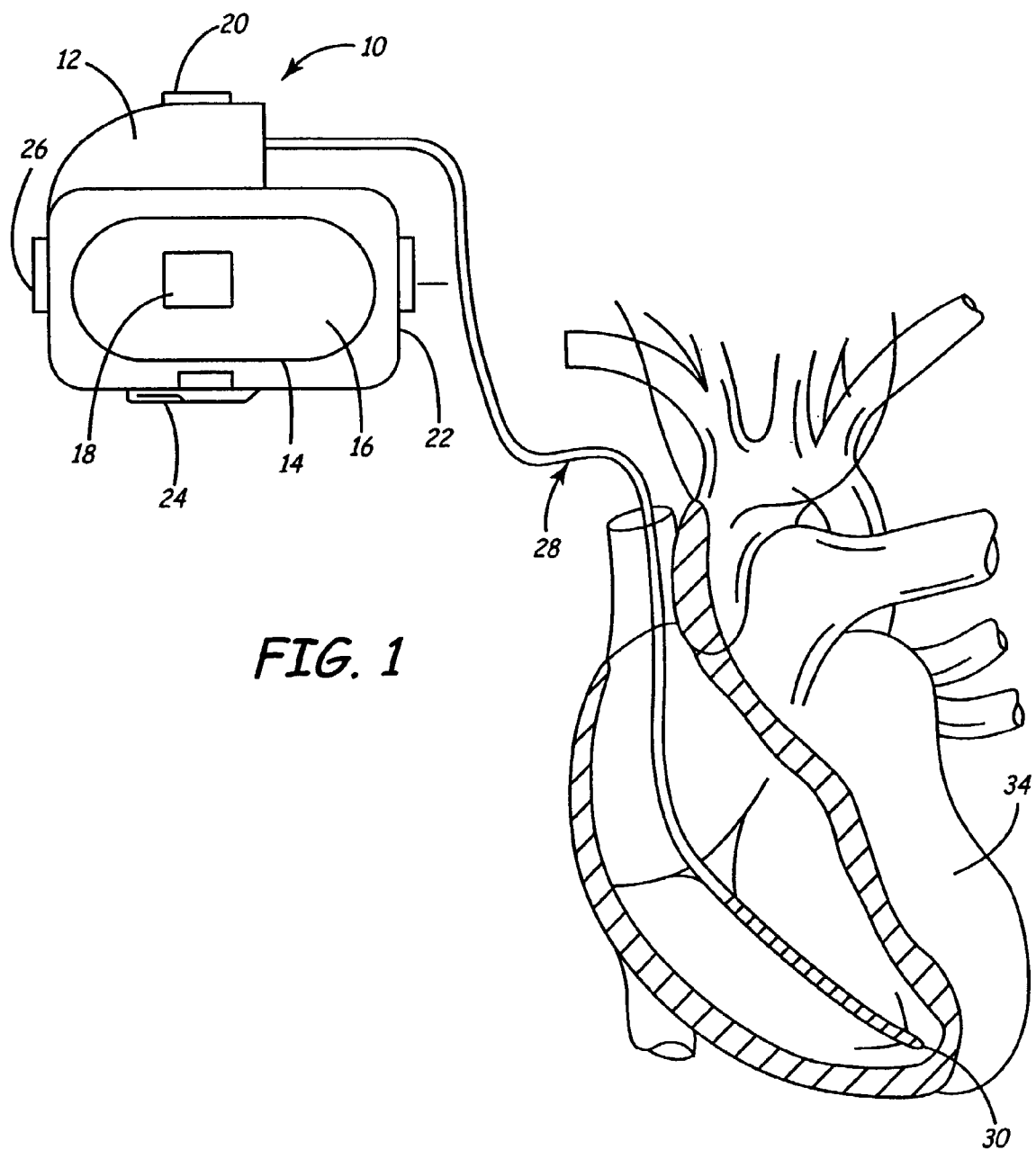
FIG. 1 is a diagram illustrating an exemplary implantable medical device in association with a heart.

FIG. 1 is a diagram illustrating an implantable medical device (IMD) 10 in association with a heart 34. IMD 10 may be configured for both monitoring and therapy of heart 34. For example, IMD 10 may include a pulse generator to deliver electrical stimulation to heart 34 for use in cardioversion or defibrillation. In accordance with the invention, IMD 10 obtains a signal indicative of dynamic mechanical activity of heart 34, and an electrical signal indicative of electrical activity of the heart.

Using both signals, i.e., the electrical signal and the signal indicative of dynamic mechanical activity, IMD 10 detects the existence of myocardial ischemia within heart 34. When both signals reveal ischemic conditions, IMD 10 indicates an ischemic episode. The signal indicative of dynamic mechanical activity corroborates the electrical signal.

If ischemia is detected, IMD 10 can be configured to deliver appropriate therapy to alleviate its effects. The therapy may include drug delivery, electrical stimulation, or both. In addition, according to some embodiments, IMD 10 may determine the location of ischemic tissue and the severity of the ischemic condition, providing more specific information that may be useful in selection of treatment.

IMD 10 may be generally flat and thin to permit subcutaneous implantation within a human body, e.g., within upper thoracic regions or the lower abdominal region. IMD 10 may include a hermetically sealed housing 14 having a connector block assembly 12 that receives the proximal ends of one or more cardiac leads for connection to circuitry enclosed within housing 14. In the example of FIG. 1, connector block assembly 12 receives a ventricular endocardial lead 28.

In some embodiments of the invention, ventricular endocardial lead 28, or other leads, may include an accelerometer to obtain a heart acceleration signal or a pressure transducer to obtain a pressure signal. In other embodiments, a pressure signal can be obtained from outside a blood vessel, e.g., with the use of implantable blood vessel cuffs as described in U.S. Pat. Nos. 6,010,477 and 6,077,277 to Miesel et al.

Also, multiple accelerometers or pressure sensors can be used to achieve sensitivity along multiple axes. For instance, if a coronary artery providing oxygen to the left side of the heart is occluded, there may be a decrease in accelerometer- or pressure sensor-indicated contractility from a left-sided lead, but not necessarily from a lead in the right ventricle. This may be particularly the case for an accelerometer lead placed on the right ventricular free wall, which is not mechanically coupled to the left ventricle, as well as a lead placed on the ventricular septum. Accordingly, multiple sensors may be desirable for enhanced sensitivity.

An accelerometer will be generally described herein for purposes of illustration. Ventricular endocardial lead 28 may be, for example, a bipolar, two wire lead equipped to sense electrical signals. An accelerometer can be incorporated adjacent a distal tip 30 of lead 28, and thereby deployed within heart 34. As will be described, housing 14 may enclose circuitry for use in analyzing the heart acceleration signal produced by the accelerometer, and electrical signals such as ECGs or EGMs obtained by IMD 10 to detect ischemia within heart 34.

To facilitate detection of electrical activity within heart 34, IMD 10 may include a plurality of EGM sense electrodes 16, 18, 20, 22, 24, 26. EGM sense electrodes 16, 18, 20, 22, 24, 26 may be arranged substantially as described in U.S. Pat. No. 6,128,526, to Stadler et al., entitled "METHOD FOR ISCHEMIA DETECTION AND APPARATUS USING SAME," the entire content of which is incorporated herein by reference. For example, electrodes 16, 18, 20, 22, 24, 26 may form a plurality of sense electrode pairs that are integrated with the exterior of housing 12 of IMD 10.

The sense electrode pairs can be used to obtain electrical signals along one or more sensing axes to formulate one or more EGM signals. The EGM signal obtained via sense electrodes 16, 18, 20, 22, 24, 26, together with the heart acceleration signal provided by an accelerometer or pressure transducer, can be used to detect ischemia, as well as the degree of ischemia and the location of ischemic tissue within heart 34. The accelerometer provides an indication of the dynamic mechanical activity of the heart, which either reinforces or negates an indication of ischemia derived from a change in the electrical signal.

As an advantage, in addition to identification of ischemia, the heart acceleration signal can be used to measure other events in different frequency ranges. For example, the heart acceleration signal may be monitored from 0 to 0.5 Hz for the patient's posture or orientation, from 1 to 5 Hz for the patient's activity, e.g., exercise, and from 5 to 100 Hz for the patient's heart acceleration. The frequency range for analysis of heart acceleration is the range useful in identification of ischemia. Thus, the accelerometer may serve multiple purposes. For example, by analyzing the pertinent frequency bands, the accelerometer may be used to detect patient activity, patent orientation, and heart acceleration.

Although not shown in FIG. 1, as is known in the art a programmer/output device equipped with an antenna can be provided for wireless communication with the IMD 10. IMD 10 may include a telemetry circuit that transmits radio frequency messages, which may include indications of isohemia and other information to such a programmer/output device. IMD 10 also may receive programming information via the telemetry circuit for modification of operational parameters within the IMD.

The programmer/output device also may include a display for graphic or textual presentation of information transmitted by IMD 10, as well as a visible or audible annunciator that provides an indication of the detection of ischemia within heart 34. IMD 10 also may be equipped with an alarm for notification of the patient in the event ischemia is detected. Also, as is known in the art a programmer/output device may include a user input device, such as a keypad, by which a physician may modify operational parameters for use in programming IMD 10 for diagnosis or treatment.

Figure 2:
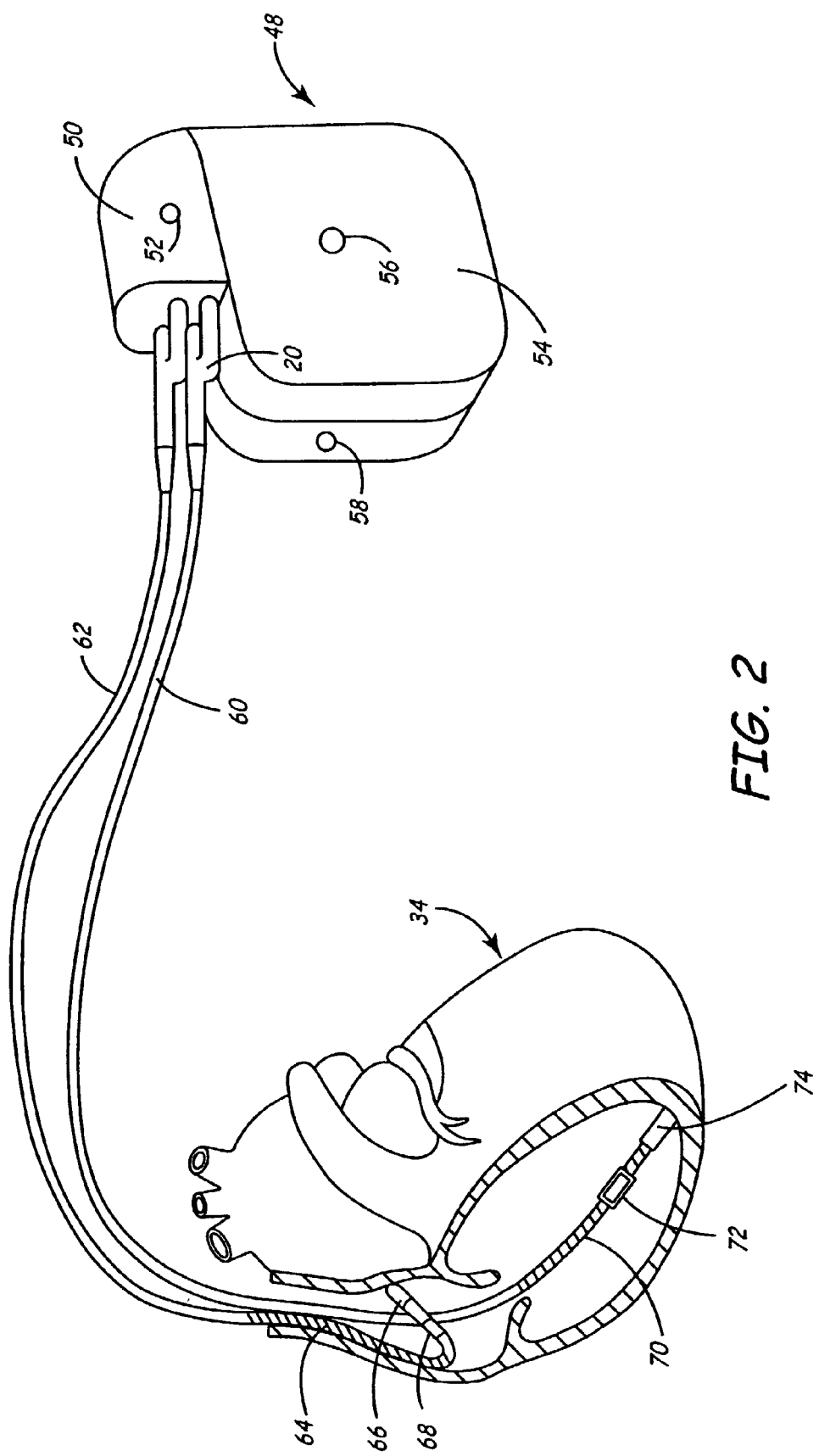
FIG. 2 is a diagram illustrating another exemplary implantable medical device in association with a heart.

FIG. 2 is a diagram illustrating another IMD 48 in association with a human heart 34. In particular, IMD 48 may be configured to provide electrical stimuli to heart 34 for defibrillation. IMD 48 may generally conform to the defibrillation system described in the above-referenced U.S. Pat. No. 6,128,526. In the example of FIG. 2, IMD 48 includes an outer housing 54 that functions as an electrode, along with a set of electrodes 52, 56, 58 provided at various locations on the housing or connector block 50.

IMD 48 may include leads 60, 62 for deployment of defibrillation coil electrodes 64, 70 within two chambers of heart 34. Leads 60, 62 may include additional electrodes, such as electrodes 66, 68, 72, 74, for sensing of electrical activity within heart 34. Electrodes 66, 68, 72, 74 may form electrode pairs with respective electrodes 52, 56, 58 on IMD 48. As in the example of FIG. 1, an accelerometer can be mounted in one of leads 60, 62 to obtain a heart acceleration signal for use in detecting ischemia. In some embodiments, the heart acceleration signal may be derived from left-sided leads deployed via the coronary sinus. Also, a pressure sensor may be used in lieu of the accelerometer in some embodiments.

FIG. 3 is a side view illustrating an implantable lead 76 equipped with a lead-tip accelerometer. Lead 76 may be configured for use as a diagnostic lead, therapeutic lead, or both, and may be incorporated with a variety of IMDs including those shown in FIGS. 1 and 2. For example, lead 76 may carry sense electrodes, stimulation electrodes, or both. As shown in FIG. 3, lead 76 may include a distal tip 78, a first section 80, and a second section 82. First and section sections 80, 82 include outer walls 81, 83, respectively, formed of nonconductive, biocompatible material.

One or more sense or stimulation electrodes may be formed along the longitudinal extent of outer walls 81, 83. Distal tip 78 may include an electrode 84, as well as a number of stabilizing tines (not shown in FIG. 3) for securing distal tip member 78 in cardiac tissue upon deployment. In addition, lead 76 may include electrical conductors which may be coupled to electrode 84 and an accelerometer assembly mounted within second section 82.

FIG. 4 is a cross-sectional side view of lead 76 shown in FIG. 3. FIG. 4 shows first section 80, second section 82, distal tip 78, electrode 84. Stabilizing tines or other anchoring structure may be added to distal tip 78, if desired. In the example of FIG. 4, lead 76 includes an accelerometer assembly 88 mounted within second section 82 adjacent distal tip 78. Accelerometer assembly 88 forms a capsule, and includes an accelerometer that may be fabricated using microelectromechanical systems (MEMS) technology, providing high tolerance and very small size. Advantageously, accelerometer assembly 88 may be used in a bipolar lead system, reducing accelerometer assembly size and increasing reliability.

Lead 76 also includes conductors in the form of first and second conductive coiled conductors 90, 92, which are arranged coaxially along the length of the lead. Coiled conductors 90, 92 may be coupled to distal electrode 84 and accelerometer assembly 88 to carry electrical current to and from the electrode and accelerometer assembly to a proximal end of the lead, which may be coupled to an IMD. For example, inner coiled conductor 90 may be coupled to interior components of accelerometer assembly 88 via a feedthrough assembly 86. Outer coiled conductor 92 may be coupled to the exterior housing of accelerometer assembly 88, which is electrically conductive and may be formed from titanium, and to electrode 84. The accelerometer signal may be produced between conductors 90, 92 via an internal accelerometer connection and the exterior housing connecting, respectively. The signal from electrode 84 may be produced between conductor 92 and an electrode on the IMD housing or "can." Distal tip 78, first section 80, and second section 82 are crimped together at crimp points indicated generally by reference numerals 94, 96, 98. An adhesive material 99 fills the void within feedthrough assembly 86.

The heart acceleration signal varies as a function of the contractile force of heart 34. The contractile force is transduced by accelerometer assembly 88 to produce an electrical heart acceleration signal that represents the contractility of the heart and, more generally, the dynamic mechanical activity of the heart. The contractile force of heart 34 physically deforms the accelerometer in assembly 88 to change its electrical properties, and modulate the current passing through the accelerometer. Again, an indication of heart contractility can be obtained alternatively using a pressure transducer.

Accelerometer assembly 88 can make use of conventional accelerometer technology and may take the form of a piezoelectric, piezoresistive, capacitive, inductive, or magnetic sensor that produces a change in an electrical property with changes in accelerometric force within heart 34. The changes in the electrical property, e.g., resistance, capacitance, inductance, and the like, in turn produces changes in the electrical signal produced by accelerometer assembly 88.

In the example of FIG. 4, accelerometer assembly 88 is mounted at the tip or distal end of lead 76. Accelerometer assembly 88 could be mounted elsewhere within lead 76, however, provided it can be properly positioned and oriented to detect accelerometric force produced by the contractile activity of heart 34. In some embodiments, accelerometer assembly 88 may be formed to have either one, two, or three detection axes. In other words, accelerometer assembly 88 may be configured to detect accelerometric force extending in multiple directions as a result of the contractile force generated by different walls within heart 34.

In this case, accelerometer assembly 88 may be equipped with a multi-axis accelerometer or multiple accelerometers oriented orthogonally in relation to the respective axes, as well as multiple conductors for obtaining the heart acceleration signal as output from each respective accelerometer. As one example, accelerometer assembly 88 could include a single conductor line that carries current to multiple accelerometers, and two or more additional conductor lines that return current from each of the accelerometers to provide separate heart acceleration signal outputs for the different axes. Alternatively, each accelerometer may be coupled to the same conductor lines, and produce signals that are time-multiplexed to distinguish the output of each accelerometer.

Detection of heart acceleration along multiple axes may be useful in determining the location of ischemic tissue. If the heart acceleration signal along one axis is "normal," i.e., not indicative of ischemia, whereas the heart acceleration signal along another axis indicates a possible episode of ischemia, the location of the ischemic tissue can be determined according to the orientation of the axis along which the pertinent accelerometer is aligned.

In this manner, the ischemic condition can be treated, by intervention of a physician or in an automated manner, and targeted to an appropriate region of heart 34. For example, based on the location of the ischemic tissue, electrical stimulation can be delivered to a selected stimulation electrode best suited for treatment of the affected location.

In addition, the amplitude, frequency, or pulse width of stimulating current can be controlled according to the affected location to achieve an optimum therapeutic effect. As a further alternative, determination of the location of ischemic tissue can be used to choose other types of therapy such as drug delivery, as well as types, dosages and durations of drug delivery. Also, the location information can be compared to location information recorded in the past to determine whether the ischemia is occurring in a new location or a location of prior ischemic episodes.

Figure 5:
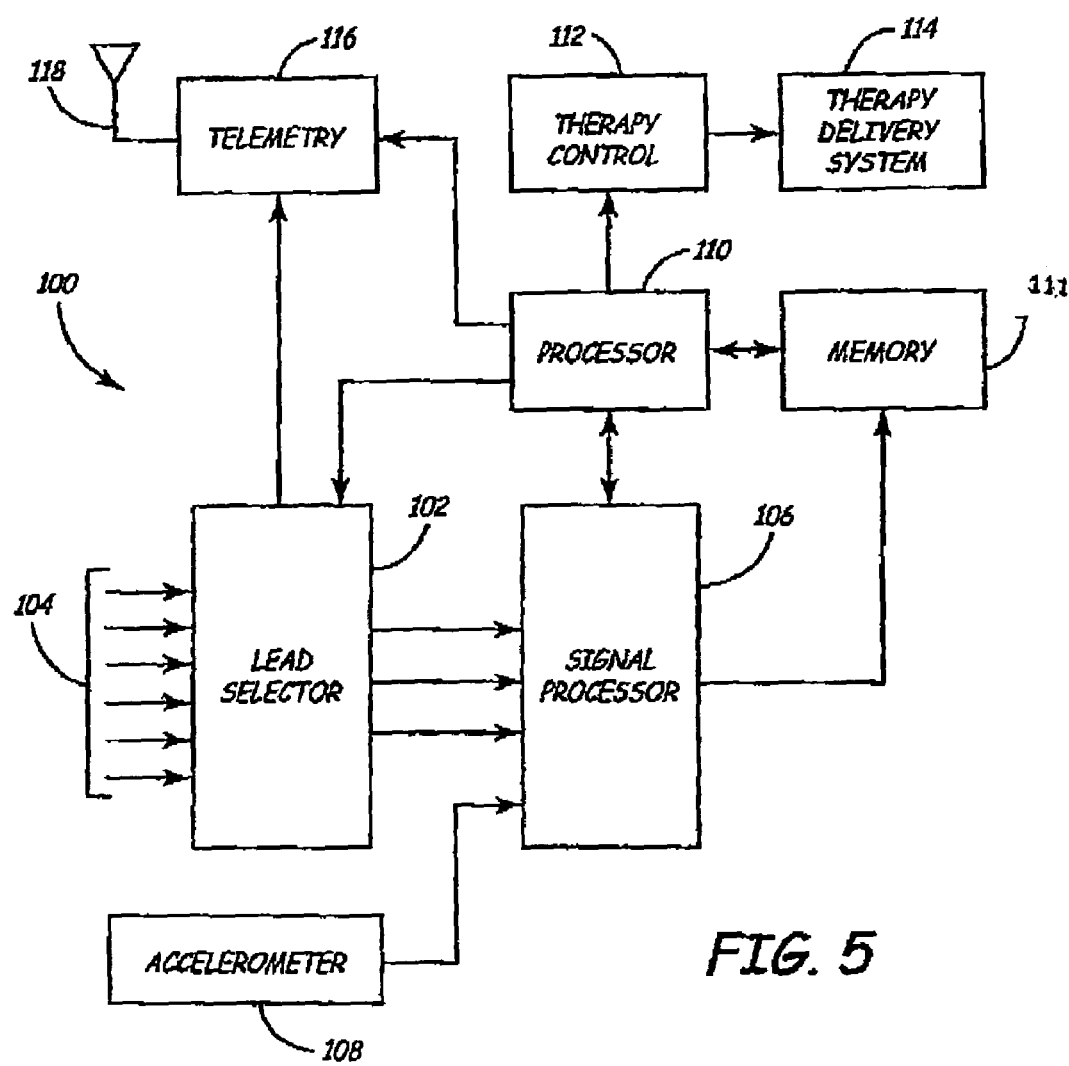
FIG. 5 is a block diagram illustrating a system for detection of ischemia.

FIG. 5 is a block diagram illustrating a system 100 for detection of isohemia. As shown in FIG. 5, system 100 may include a lead selector circuit 102 that selects one or more lead pairs 104, a signal processor circuit 106, an accelerometer 108, a processor 110, memory 111, a therapy control circuit 112, a therapy delivery system 114, and a telemetry device 116 with an antenna 118. Lead selector circuit 102 may be controlled by processor 110, and select lead pairs for acquisition of electrical signals oriented along multiple detection axes relative to heart 34.

Processor 110 may take the form of a microprocessor, microcontroller, digital signal processor (DSP) or other programmable logic device. The electrical signals obtained via the lead pairs can be used to formulate an ECG or EGM for analysis of the PQRST complex and, in particular, the ST segment. Changes in the ST segment can be an indicator of ischemia. Analysis of the dynamic mechanical activity of the heart in combination with changes in the ST segment, according to the invention, can provide a more reliable indication of ischemia.

Signal processor circuit 106 receives the output of lead selector circuit 102 and a heart acceleration signal from an accelerometer 108, which may be deployed in a lead tip as described with reference to FIGS. 3 and 4. In other embodiments, signal processor circuit 106 may receive a pressure signal from a pressure transducer. The output of lead selector circuit 102 may be three electrode pair signals, such as RV coil-can, RV ring-can, and SVC coil-can. In some embodiments, as discussed above, accelerometer 108 may produce multiple heart acceleration signals oriented along similar detection axes. Signal processor circuit 106 may include a number of sense amplifiers that amplify the ECG or EGM signals, as well as the heart acceleration signal.

In addition, signal processor circuit 106 may include sampling and comparator circuitry for analysis of the electrical signals and heart acceleration signals relative to criteria such as average, peak-to-peak, or total amplitude thresholds. Alternatively, processor 110 may digitally sample the signals amplified by signal processor circuit 106 and perform a software-based analysis of the digital signals. Thus, signal processor circuit 106 may include an analog-to-digital converter that converts the analog signals produced by lead selector circuit 102 and accelerometer 108 into digital samples for analysis by processor 110. Processor 110 may provide the necessary control and clock signals for operation of signal processor circuit 106.

A memory 111 is provided for storage of digital samples produced by signal processor circuit 106 and intermediate data stored and retrieved by processor 110. For example, signal processor circuit 106 may include a number of buffers that hold digital samples for storage in memory. Although not illustrated in FIG. 5 for simplicity, processor 110, memory 111, and signal processor 106 may communicate via a common data and instruction bus, as is well known in the art. The digital samples may be parameterized, in signal processor circuit 106 or processor 110, to produce values for comparison to a predetermined threshold. Again, the comparison may take place within discrete circuitry provided by signal processor circuit 106 or via code executed by processor 110. The code may include instructions carried by a computer-readable medium accessible by processor 110, such as memory 111 or other fixed or removable media devices associated with an external programmer/output device communicatively coupled to the processor via telemetry device 116.

ECG, EGM, SEA or other electrical signals produced by lead selector circuit 102 can be processed and parameterized to represent a variety of different values useful in the comparison. In one embodiment, the electrical signals may be processed to produce an amplitude value, such as an average, peak-to-peak, or total amplitude, for the ST segment of the PQRST complex. The ST segment is typically close in amplitude to the baseline of the ECG or EGM signal sensed between consecutive PQRST sequences. During episodes of myocardial ischemia, however, the ST segment amplitude may increase or decrease substantially. Thus, by comparing the amplitude of the ST segment to an amplitude threshold, processor 110 can identify a potential episode of ischemia.

In addition, processor 110 may be configured to detect a location of the ischemic condition based on which one of the lead pairs produces an ST segment excursion above the amplitude threshold. In some embodiments, the location may be correlated with one of several acceleration signals obtained from accelerometer 108 for different sensing axes.

An average amplitude may be obtained and represented in a number of ways such as by computing the average of a series of samples over the period of time coincident with the ST segment. A peak-to-peak amplitude for each signal can be obtained by detection of maxima and minima of the ST segment and detection of maxima and minima of a heart acceleration signal over a duration of time that generally coincides with the ST segment. A total amplitude for each signal can be obtained by integrating the ST segment and integrating the acceleration signal over a duration of time that generally coincides with the ST segment. Also, because the change in the ST segment may be elevated or depressed during an ischemic episode, the ST segment parameter may rely on the absolute value of the change in the ST segment.

Because the use of the ST segment as an indicator of ischemia can be unreliable, processor 110 (and/or signal processor circuit 106) is also configured to analyze the heart acceleration signal produced by accelerometer 108. In particular, processor 110 compares a parameterized value representative of the heart acceleration signal, such as an average amplitude or integrated amplitude, at a time substantially coincident with the ST segment to a pertinent threshold. In this manner, system 100 is capable of correlating the ST segment and the heart acceleration signal for more reliable detection of ischemia.

By verifying whether the heart acceleration signal (or alternatively a pressure signal) also indicates ischemia, processor 110 is able to disregard deviations in the ST segments due to conditions other than ischemia, e.g., due to changes in the overall PQRST complex caused by axis shifts, electrical noise, cardiac pacing stimuli, drugs, and high sinus or tachycardia rates that distort the PQRST complex. Consequently, system 100 is capable of reducing the number of false indications of ischemia, and increasing the reliability of the ST segment as an indicator of myocardial ischemia.

Based on deviation of the ST segment and the heart acceleration signal relative to the pertinent thresholds, processor 110 also may quantify the severity of the ischemic condition. If the ST segment and the heart acceleration signal both satisfy the pertinent thresholds, processor 110 indicates an ischemic event, and may be programmed to effect therapeutic action. For example, processor 110 may generate a therapy control signal that causes a therapy control circuit 112 to request delivery of therapy from a therapy delivery system 114. Therapy delivery system 114 may take, for example, the form of a drug delivery system or electrical stimulation system such as a cardioversion or defibrillation circuit.

Processor 110 also may indicate to therapy control circuit 112 the location of the ischemic tissue and the severity of the ischemic condition based on the accelerometer signal. Accordingly, therapy control circuit 112 may be configured to control therapy delivery system 114 based on the indications provided by processor 110. For example, therapy control circuit 112 may select the type of therapy, e.g., drug delivery and/or electrical stimulation, the dosage, amplitude, and duration of the therapy, as well as the location for delivery of the therapy, based on the indications of location and severity provided by processor 110.

Processor 110 also may control a telemetry device 116 to communicate an indication of the ischemic condition to an external device via antenna 118. Thus, the indication may be a wireless, radio frequency message that indicates an ischemic condition and, in some embodiments, the location of the ischemic tissue and the severity of the ischemic condition. In addition, the IMD itself may have an audible alarm that notifies the patient when an ischemic episode is occurring.

The external device, which may be a programmer/output device, advises a physician or other attendant of the ischemic condition, e.g., via a display or a visible or audible alarm. Also, the ischemic events may be stored in memory in the external device, or within the IMD, for review by a physician. The components of system 100, with the exception of accelerometer 108 and leads 104, may be housed in a common housing such as those shown in FIGS. 1 and 2. Alternatively, portions of system 100 may be housed separately. For example, therapy delivery system 114 could be provided in a separate housing, particularly where the therapy delivery system includes drug delivery capabilities. In this case, therapy control circuit 112 may interact with therapy delivery system 114 via an electrical cable or wireless link.

Figure 6A:
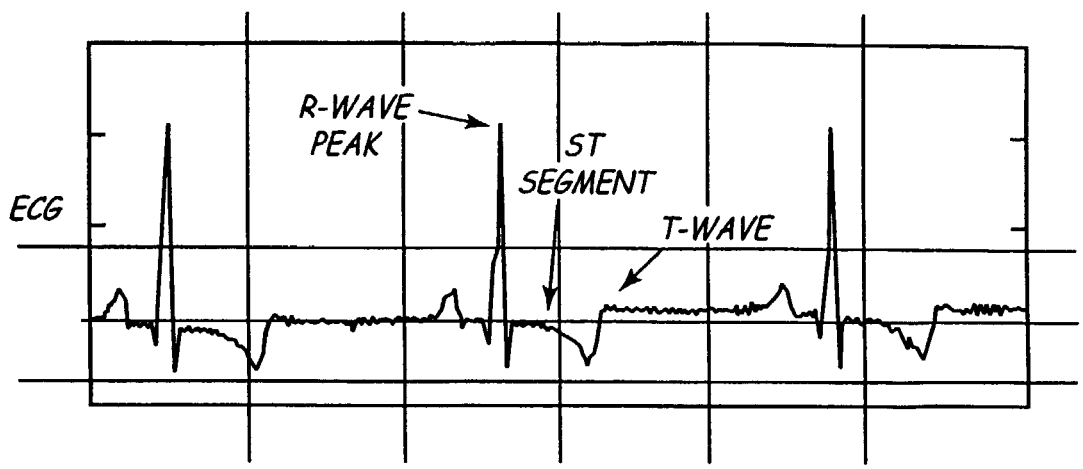
FIGS. 6A, 6B, and 6C are graphs illustrating the relationship between electrical activity and heart acceleration within a canine heart.
Figure 6B:
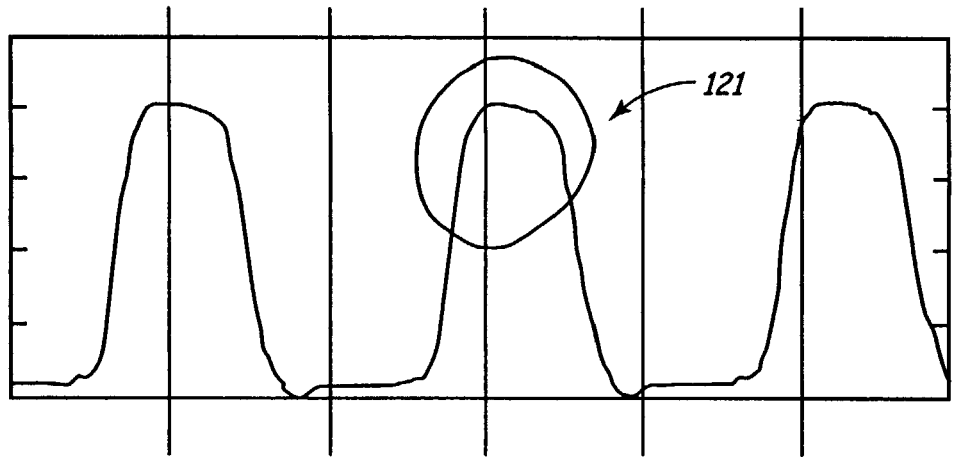
Figure 6C:
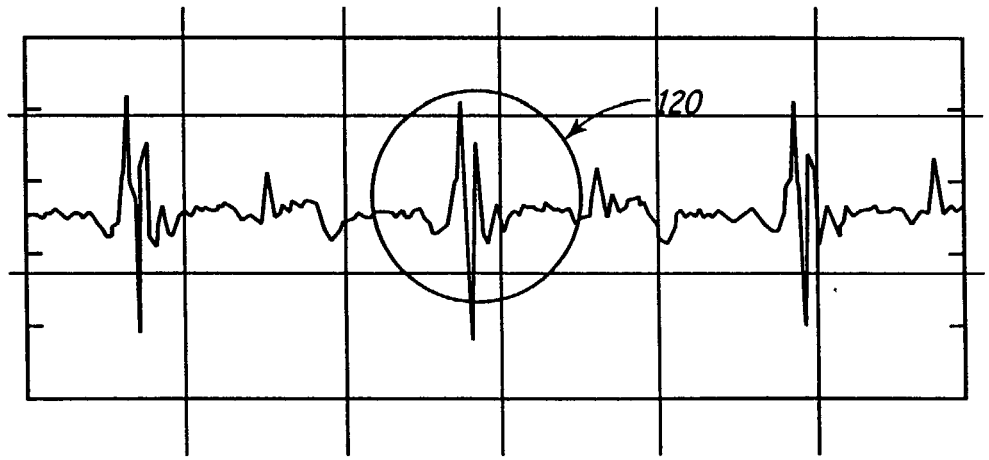

FIGS. 6A, 6B, and 6C are graphs illustrating an example relationship between electrical activity and heart acceleration within a canine heart. In particular, FIG. 6A shows an ECG signal, including the R-wave peak, ST segment and T-wave over a period of time. FIG. 6B shows the output of a pressure sensor positioned within the left ventricle, e.g., in a lead deployed within the ventricle, over the same period of time. FIG. 6C shows the output of an accelerometer positioned within the right ventricle, e.g., at the tip of a lead deployed within the ventricle, also over the same period of time.

The heart acceleration signal is characterized by a section 120 that generally coincides in time with the ST segment of the ECG signal. Similarly, the pressure signal has a section 121 that coincides with the ST segment. In this example, sections 120, 121 are characterized by a momentary positive excursion followed by a negative excursion, which correspond to the contractile forces of the left ventricle. The increase in pressure is due to the pressure developed during contraction. The pressure drops during relaxation. For the acceleration signal, the increase is due to the heart's acceleration or vibration during contraction, with the acceleration signal occurring during the same time as the maximum slope of the pressure signal (DP/DT). A second acceleration signal, typically of a lower amplitude than the first acceleration signal and corresponding to the maximum negative DP/DT, also can be seen. The waveforms may vary significantly, however, depending on the location of the lead, the accelerometer sensitivity axis, and other factors.

FIGS. 6A and 6C also illustrate example amplitude thresholds T1 and T2. The thresholds may be used in analysis of the ST segment amplitude and heart acceleration signal amplitude, respectively. A similar threshold can be used for the pressure signal. The thresholds may reflect an average amplitude over the duration of the ST segment or a peak-to-peak amplitude. As an alternative, total amplitudes obtained, e.g., by integration of the heart acceleration signal, could be used for comparison to total amplitude thresholds. In the example of FIGS. 6A–6C, thresholds T1 and T2 represent peak-to-peak amplitude thresholds for comparison to the maxima and minima of the ST segment and heart acceleration signal, respectively.

Figure 7A:
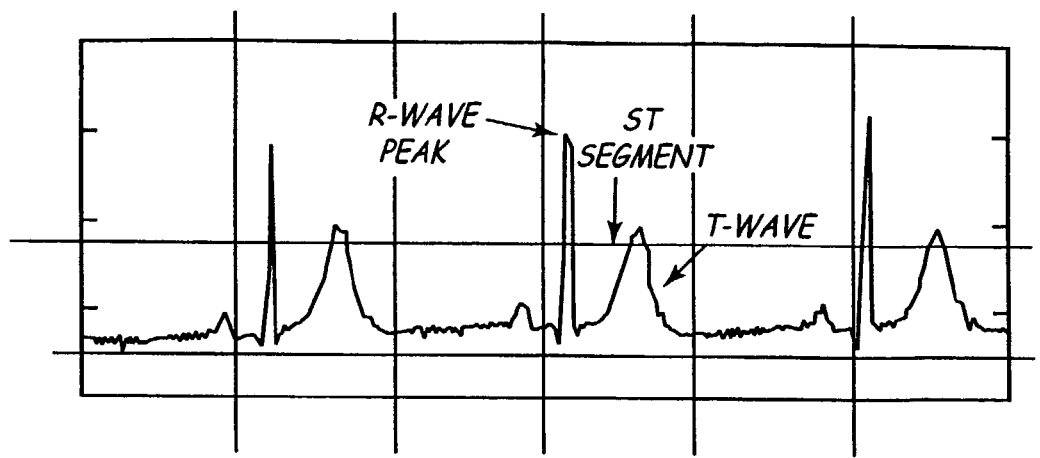
FIGS. 7A, 7B, and 7C are graphs illustrating the relationship between electrical activity and heart acceleration within a canine heart during an episode of ischemia.
Figure 7B:
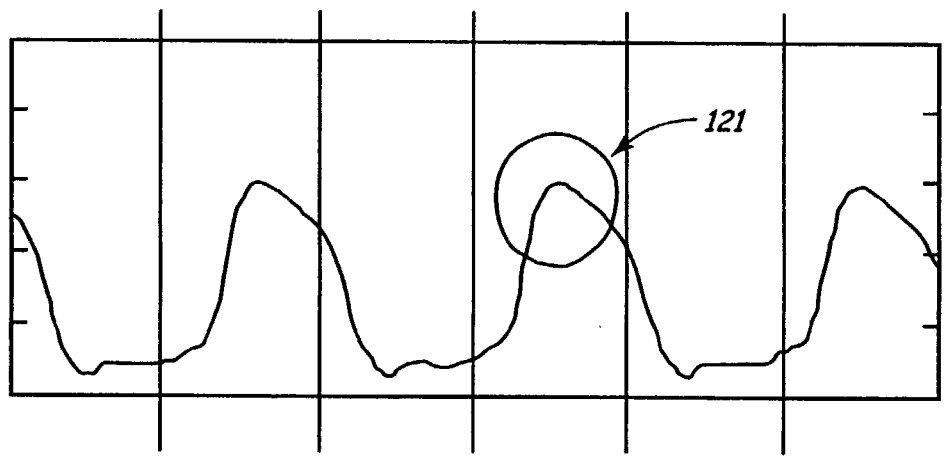
Figure 7C:
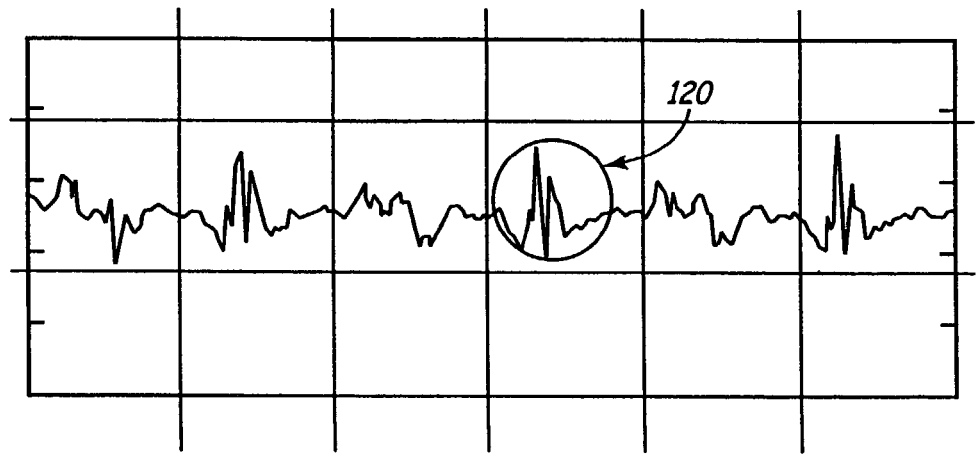

FIGS. 7A, 7B, and 7C are graphs illustrating an example relationship between electrical activity and heart acceleration within a canine heart during an episode of ischemia. As shown in FIG. 7A, the ST segment of an ECG or EGM signal may show a significant increase when the heart tissue becomes ischemic. In comparison to FIG. 6A, for example, the amplitude of the ST segment in FIG. 7A is markedly increased, and exceeds the threshold T1, which may be specified by a physician for identification of ischemic conditions. In FIG. 7B, the amplitude of the pressure signal is decreased relative to that shown in FIG. 6B.

As shown in FIG. 7C, the heart acceleration signal also shows the effects of ischemia. Specifically, in a case of ischemia, the section 120 of the heart acceleration signal that coincides with the ST segment is markedly decreased in amplitude relative to FIG. 6C. In this example, section 120 has a peak-to-peak amplitude that is less than the threshold T2. Thus, when the amplitude of the ST segment exceeds threshold T1 and the amplitude of the heart acceleration signal drops below threshold T2, an episode of ischemia can be more reliably indicated in accordance with the invention.

Again, the amplitudes of the ST segment and heart acceleration signal, as well as the thresholds T1 and T2, may be peak-to-peak, average, or total amplitudes, or any other parameter deemed reliable in detection of ischemia. The basic technique simply involves analysis of both the ST segment and the heart acceleration signal in a correlative manner to reduce the possibility that changes in the ST segment are due to factors other than ischemia. This enables a reduction in the number of false indications.

Figure 8:
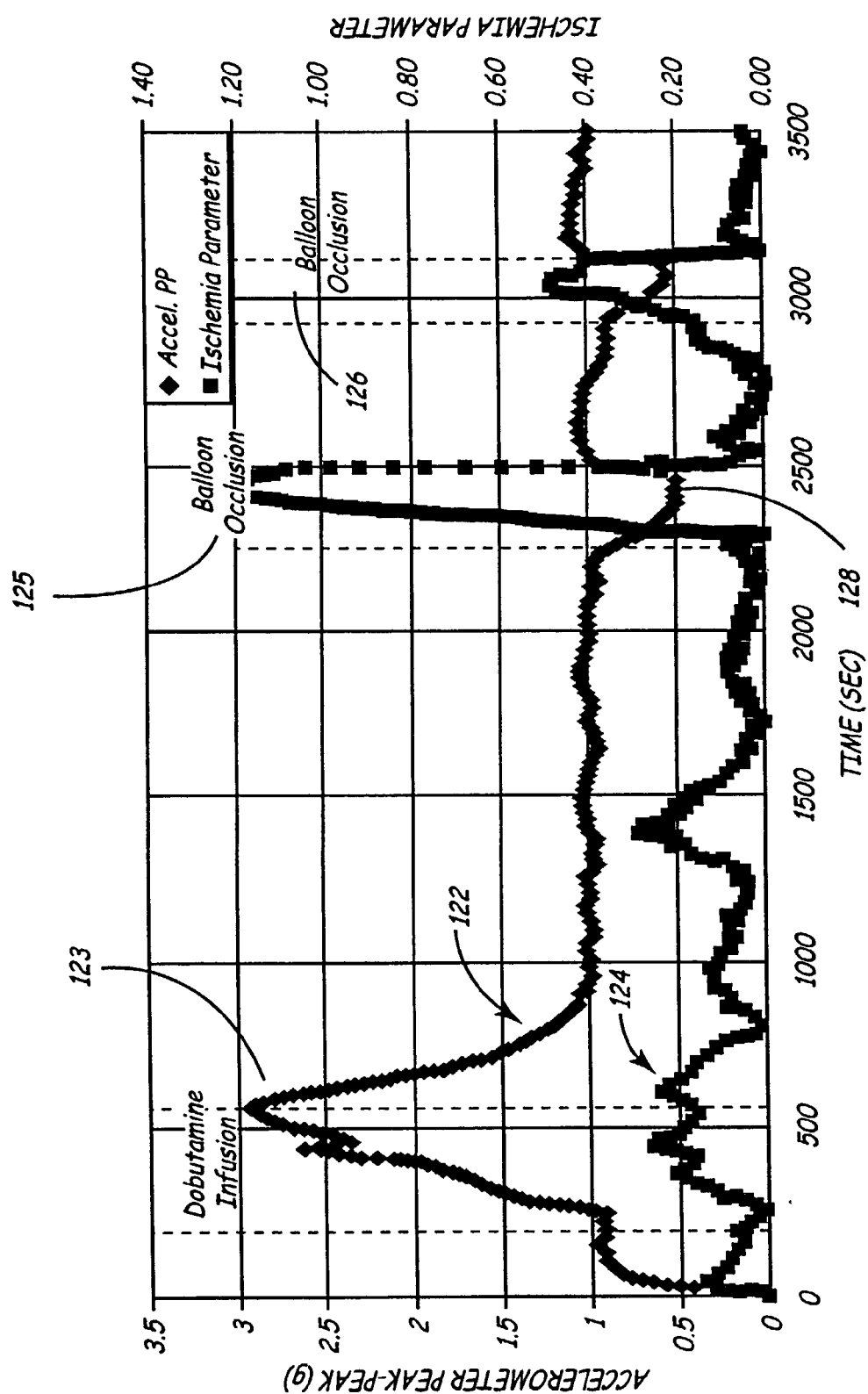
FIG. 8 is another graph illustrating changes in heart acceleration in the presence of ischemia.

FIG. 8 is another graph illustrating changes in heart acceleration in the presence of ischemia. In particular, FIG. 8 illustrates changes in the heart acceleration signal 122 during an experiment in which ischemia is induced in a canine heart. The left axis of the graph shows the accelerometer peak-to-peak signal, measured in gravitational g's. The bottom axis shows the progression of time. The right axis shows an ischemia parameter 124. The ischemia parameter 124 can be derived from, for example, an electrical signal such as the ST segment of an ECG or EGM signal. In particular, ischemia parameter 124 may represent the ST segment change as a percentage of the R-wave amplitude.

As shown in FIG. 8, following a dobutamine infusion 123, the heart acceleration signal 122 peaks sharply, as the dobutamine induces a forceful contraction in the heart. Later, the heart is subjected to balloon occlusion to intentionally limit the flow of blood, and thereby induce ischemia. At that time, the ischemia parameter peaks sharply, as indicated by reference numeral 125, whereas the heart acceleration signal 122 drops noticeably, as indicated by reference numeral 128. When the balloon occlusion is again applied, as indicated by reference numeral 126, the heart acceleration signal 122 again drops while the ischemia parameter peaks. The vertical dashed lines in FIG. 8 denote the duration of the dobutamine infusion, first balloon occlusion, and second balloon occlusion.

Figure 9:
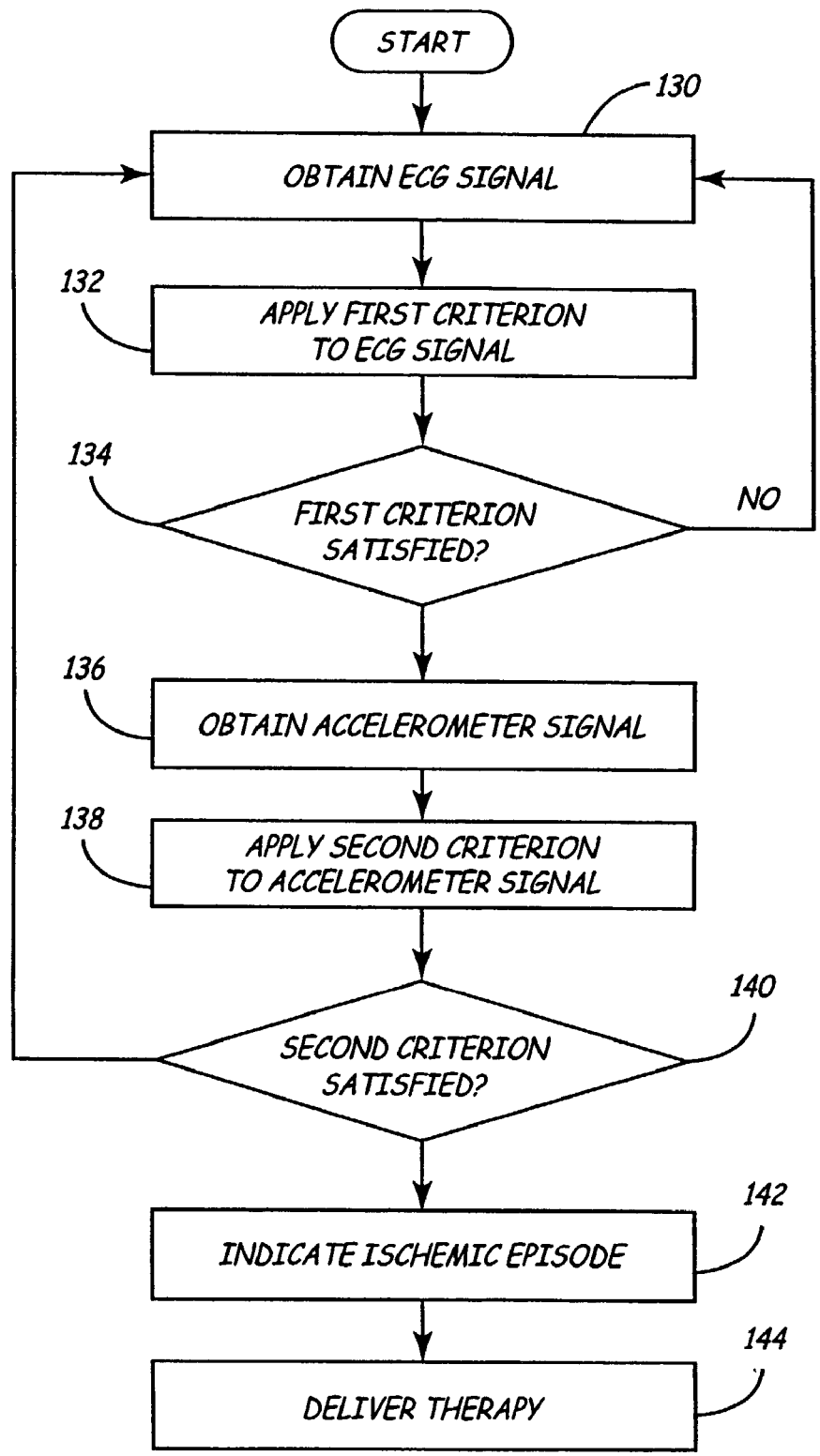
FIG. 9 is a flow diagram illustrating a process for ischemia detection.

FIG. 9 is a flow diagram illustrating a process for ischemia detection. In general, the process may include obtaining an electrical signal such as an ECG or EGM signal (130) and applying a first criterion to the signal (132). For example, the first criterion may be an amplitude threshold that is compared to an amplitude parameter of the electrical signal, such as an average, peak-to-peak or total amplitude of the ST segment of the electrical signal. If the first criterion is not satisfied, the process returns to evaluation of the electrical signal (130).

If the first criterion is satisfied (134), the technique involves obtaining an accelerometer signal, i.e., a heart acceleration signal (136), and applying a second criterion to the accelerometer signal (138). The second criterion, like the first criterion, may be an amplitude threshold that is compared to an amplitude parameter of the heart acceleration signal, such as an average, peak-to-peak, or total amplitude in a region that temporally coincides with the ST segment of the electrical signal.

If the second criterion is not satisfied, the process returns to evaluation of the electrical signal (130). If the second criterion is satisfied (140), however, the process indicates an ischemic episode (142). In some embodiments, the process may respond to an indication of ischemia by delivering therapy to the patient (144). For example, the process may involve drug delivery or electrical stimulation. The drug delivery and electrical stimulation may be delivered by an implantable medical device, including one that is integrated with ischemia detection circuitry. Alternatively, drug delivery and electrical stimulation may be administered to the patient externally.

Figure 10:
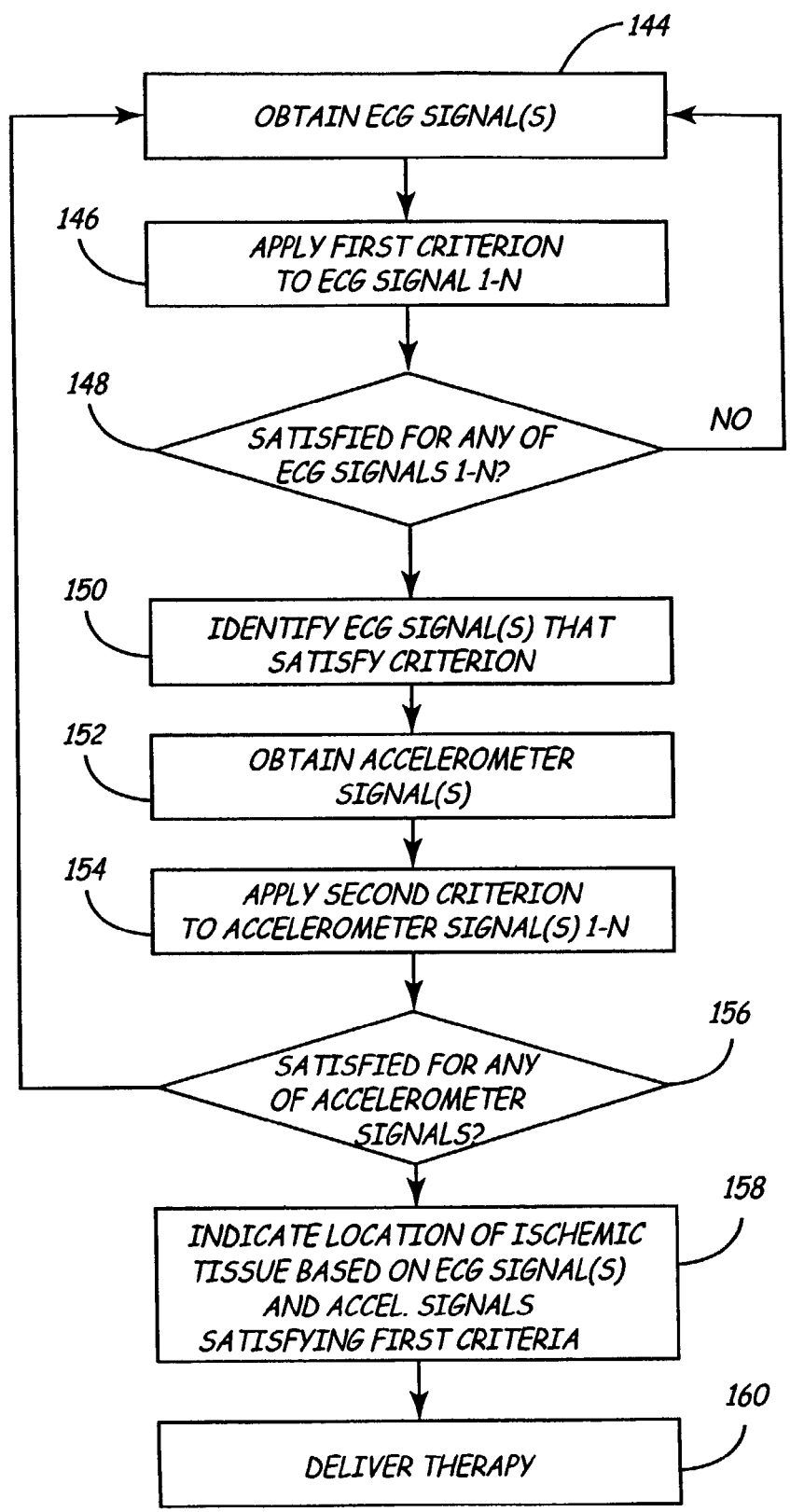
FIG. 10 is a flow diagram illustrating another process for ischemia detection.

FIG. 10 is a flow diagram illustrating another process for ischemia detection. The process of FIG. 10 is similar to that of FIG. 9, but illustrates the acquisition of multiple electrical signals for different axes to facilitate determination of the location of ischemic tissue. In particular, the process may involve obtaining multiple ECG signals (144), applying a first criterion to the signals (146), and determining whether the criterion is satisfied for any of the signals (148). If so, the process identifies the electrical signals that satisfy the criterion (150), and then obtains the accelerometer signal (152).

Upon application of a second criterion to the accelerometer signal (154), and satisfaction of that criterion (156), the process indicates an episode of ischemia along with an indication of the location of ischemic tissue based on which of the electrical signals satisfied the first criterion (158), i.e., which of the electrical signals showed a change in the ST segment indicative of ischemia. On this basis, the process may further involve delivery of therapy (160) and, in some embodiments, delivery of therapy to a particular location within the heart, or in a form selected for a particular location.

Determination of the location of ischemic tissue within the heart also can be aided by obtaining multiple heart acceleration signals along multiple axes. Like the electrical signals, the heart acceleration signals may indicate ischemia along one axis but not necessarily the others, enabling isolation of more specific region of ischemia within the heart. As with the electrical signals, this may aid in selection of the type, level, and focus of the therapy delivered to the patient.

Figure 11:
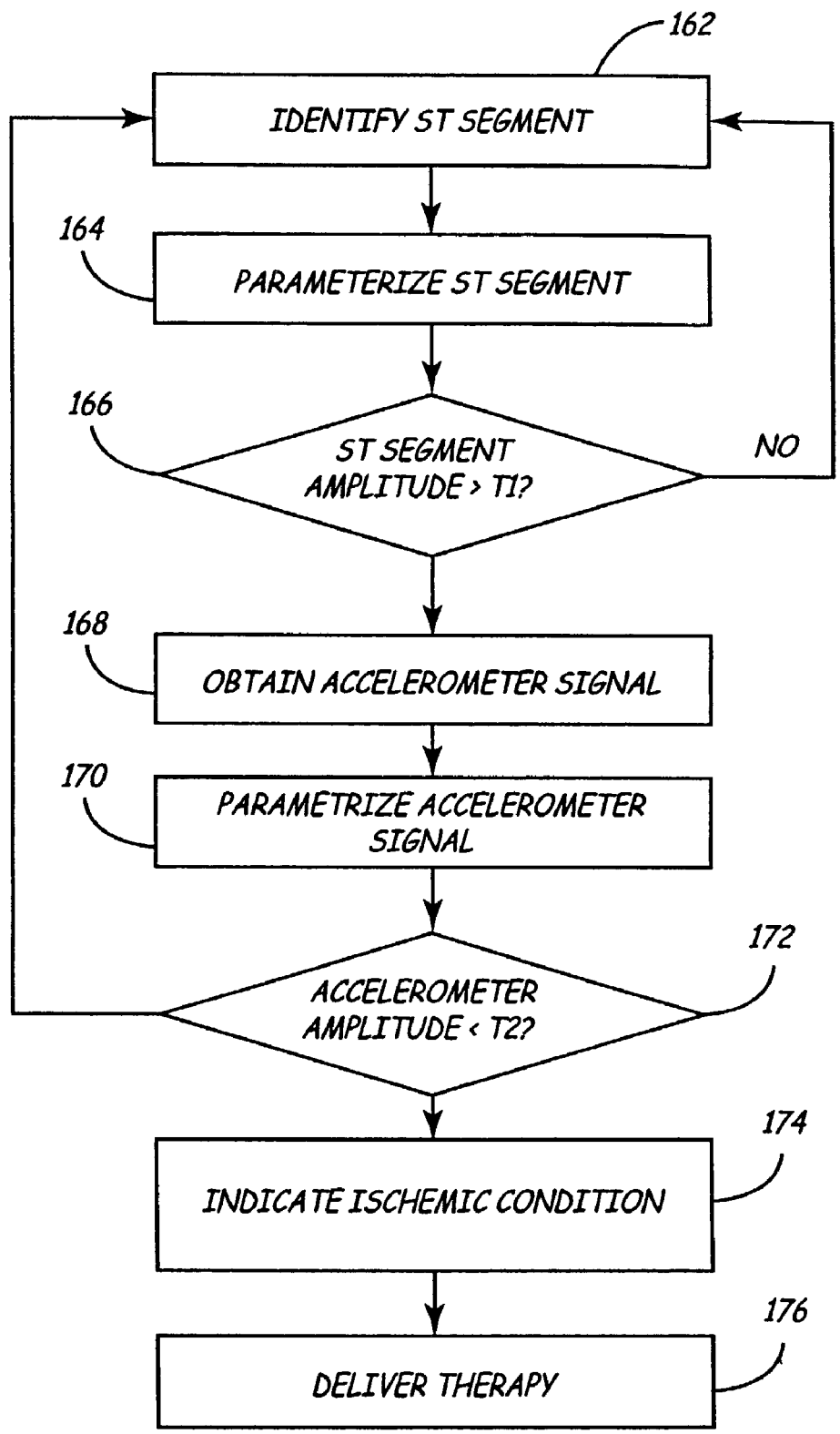
FIG. 11 is a flow diagram illustrating a process for ischemia detection in greater detail.

FIG. 11 is a flow diagram illustrating a process for ischemia detection in greater detail. As shown in FIG. 11, the process may involve analysis of an electrical signal such as an ECG or EGM signal to identify the ST segment (162). The ST segment may be parameterized (164), e.g., as a peak-to-peak amplitude, average amplitude, or total amplitude, and compared to an amplitude threshold T1 (166). If the ST segment amplitude exceeds the threshold T1, there is a potential ischemic condition.

To more reliably confirm the ischemia, the process involves obtaining an accelerometer signal (168), parameterizing the accelerometer signal (170), and comparing it to an amplitude threshold T2 (172). If the accelerometer signal amplitude drops below the threshold T2 (172), a contractility change is confirmed in addition to the increase in the ST segment, providing a more reliable indication of ischemia. On this basis, the process indicates an ischemic condition (174) and may use the indication as the basis for delivery of therapy (176) to the patient.

Amplitude thresholds are described herein for purposes of example, and are not to be read as limiting of the invention as broadly claimed. Other signal parameters may be appropriate for evaluation in identifying ischemia. Also, it is noted that exceeding a given threshold may refer to a change that results in an increase above or below a certain level, for example, as described with reference to the graphs of FIGS. 6, 7, and 8. Specifically, in some cases, ischemia may be indicated by an increase in the ST segment amplitude and a decrease in the heart acceleration signal at the time of the ST segment. Also, in some embodiments, the electrical and acceleration signals could be combined into a single parameterized value that is compared to a single threshold value to determine whether an ischemic episode is indicated.

The use of a signal indicative of dynamic mechanical heart activity to confirm an episode of ischemia indicated by the ST segment of an electrical signal can provide a number of advantages including more reliable indication of ischemia, avoidance of false indications and unnecessary administration of treatment. In addition, the heart acceleration signal may be useful, alone or in combination with the electrical signal, in more reliably quantifying the contractile function of the heart, and hence the degree of ischemia, providing a standard for the type or amount of therapy delivered to the patient.

In addition, a multi-dimensional heart acceleration signal, alone or in combination with the electrical signal, can be used to better identify the location of ischemic tissue. In effect, the use of a multi-axial accelerometer in a lead tip can detect axis shift due to postural changes and add sensitivity to the ischemia detection. The multi-axial accelerometer signals can be combined in a logical OR fashion to increase sensitivity to ischemia, or combined in a logical AND fashion to increase specificity, i.e., in terms of the location of the ischemic tissue. In addition, relative changes in the orthogonal accelerometer signals can be used to more narrowly identify the location of ischemic tissue.

In addition to the foregoing, the inventors hereof have discovered that endocardial acceleration measurements may be used as a method to track changes in global cardiac contractility. Thus, one may measure changes in peak endocardial acceleration (PEA) and left ventricular dP/dt (LV dP/dt) as a function of heart failure (HF) progression.

EMPIRICAL EXAMPLE

In at least one empirical study of the use of PEA as a function of HF progression utilized the following protocol: Four canines were chronically instrumented with a custom LV pressure sensor (which comprised an endocardial single-axis accelerometer lead in the RV apex) although other pressure sensors may be used as will be readily appreciated by those of skill in the art. A high rate (HR) pacemaker was connected to LV epicardial bipolar pacing electrodes.

Of course, although a single-axis accelerometer was utilized in this empirical example more than one single-axis accelerometer may be utilized or, in lieu of or addition to a single-axis accelerometer a multi-axis accelerometer may be employed. That is, one or more dual-or triple-axis accelerometers may be used in lieu of any particular single-axis accelerometer described with respect to the present invention.

Continuing with the empirical example, the inventors defined PEA as the peak-to-peak change in accelerometer signal measured 100 ms after the R-wave was detected. The subjects were LV paced (240 ppm) to HF (stage 3) as assessed by echocardiographic and hemodynamic measurements. LV dp/dt and PEA during sinus and LV paced rhythms were collected during unanesthetized awake monitors before and during four weeks of HR pacing.

The results were very promising (see Table 1 reproduced immediately below); that is, contractility as measured by LV dp/dt decreased by 50% ($p<0.05$) in HF for both sinus and paced rhythms. PEA was not different between the control and HF in sinus rhythm due to the high beat-to-beat variability in PEA. PEA was decreased by about 50% between control and HF in paced rhythm ($p<0.05$).

At least one conclusion may be drawn from the foregoing; that is, PEA may be used as a surrogate for LV dp/dt to assess changes in global contractility during paced rhythm.

TABLE 1

| | Hemodynamic Data Mean (SD) | | | | | |
| --- | --- | --- | --- | --- | --- | --- |
| | Heart Rate | Sinus LV dp/dt | PEA | Pacing Heart Rate | LV dp/dt | PEA |
| Control | 107(15) | 2818 (1060) | 1.1(0.4) | 206(36) | 2319 (718) | 2.0(0.7) |
| HF | 117(21) | 1352 (335)* | 0.7(0.2) | 206(36) | 1110 (320)* | 0.9(0.5)* |

*p < 0.05 vs. Control, paired t-test with Bonferroni correction

Various embodiments of the invention have been described. Alternative embodiments are conceivable. Rather than an accelerometer, for example, other sensors such as the pressure transducer described herein may be employed to obtain a signal indicative of cardiac contractility. Additionally, the maximum value of the first derivative of the pressure signal, often called the maximum DP/DT, can be used to assess the cardiac contractility and be used a signal indicative of ischemia, as can PEA. In particular, a blood pressure or velocity transducer may provide a signal useful in deriving a measure of cardiac contractility. These and other embodiments are within the scope of the following claims.

What invention claimed is:

1. A method for detecting myocardial ischemia, the method comprising by:
   obtaining a first signal indicative of dynamic mechanical activity of a heart;
   obtaining a second signal indicative of electrical activity of the heart;
   detecting a myocardial isehemia condition based on both the first signal and the second signal;
   storing a peak endocardial acceleration value in a computer memory location;
   after a predetermined time interval, obtaining at least one new peak endocardial acceleration value;
   storing the at least one new peak endocardial acceleration signal; and
   comparing the peak endocardial acceleration to the at least one new peak endocardial acceleration value;
   wherein obtaining the first signal includes obtaining a heart acceleration signal from an accelerometer deployed within the heart and wherein said heart acceleration signal is a peak endocardial acceleration value.

2. A method according to claim 1, wherein the first signal and the second signal both satisfy criteria for indication of ischemia.

3. A method according to claim 2, wherein the criteria include a change in the first signal having a first predetermined relationship to a first threshold and a change in the second signal having second predetermined relationship to a second threshold.

4. A method according to claim 1, wherein said accelerometer is deployed spaced from an adjacent portion of endocardial tissue.

5. A method according to claim 4, wherein said adjacent portion of endocardial tissue is a one of the following: a portion of transseptal tissue, a portion of right ventricle tissue, a portion of ventricular outflow tract tissue, a portion of left ventricle tissue.

6. The method of claim 1, further comprising, when myocardial ischemia is detected, generating a signal for delivery of therapy to alleviate effects of the ischemia within the heart.

7. A method according to claim 1, wherein said accelerometer is a multiple axis accelerometer.

8. A computer readable medium for storing computer executable instructions for performing a method for detecting myocardial ischemia, comprising:
   executable instructions for obtaining a first signal indicative of dynamic mechanical activity of a heart from an accelerometer sensor;
   executable instructions for obtaining a second signal indicative of electrical activity of the heart;
   executable instructions for detecting a myocardial ischemia condition based on both the first signal and the second signal;
   executable instructions for storing the peak endocardial acceleration value in a computer memory location;
   executable instructions for, after a predetermined time interval, obtaining at least one new peak endocardial acceleration value;
   executable instructions for storing the at least one new peak endocardial acceleration signal; and
   executable instructions for comparing the peak endocardial acceleration to the at least one new peak endocardial acceleration value
   wherein the executable instructions for obtaining the first signal further comprises a instructions for obtaining a heart acceleration signal from the accelerometer sensor wherein said accelerometer sensor is deployed within a chamber of the heart and wherein said heart acceleration signal is a peak endocardial acceleration value having a value over a dynamic range of about 5 Hz to about 100 Hz.

9. A computer readable medium according to claim 8, further comprising, when myocardial ischemia is detected, executable instructions for storing information about the myocardial ischemia in a computer memory storage location.

10. A computer readable medium according to claim 9, further comprising, when myocardial ischemia is detected, executable instructions for delivering therapy to a patient including at least one of: a drug delivery therapy, an electrical stimulation therapy, a modification of ongoing electrical stimulation therapy, a combination of a drug delivery therapy and an electrical stimulation therapy.

11. A computer readable medium according to claim 8, wherein the executable instructions for obtaining the first signal further comprises instructions for obtaining a heart acceleration signal from the accelerometer wherein said accelerometer sensor is integrated into an end portion of an implanted medical lead.

12. A computer readable medium according to claim 11, wherein the lead is a therapeutic lead coupled to an implanted medical device for delivery of electrical stimulation to the patient.

13. A computer readable medium of claim 11, wherein the lead is a diagnostic lead coupled to an implanted medical device for acquisition of diagnostic data.

14. A computer readable medium according to claim 8, further comprising instructions for obtaining the second signal from a subcutaneous electrode array.

* * * * *